United States Patent [19]

Gumprecht

[11] Patent Number: 5,051,538
[45] Date of Patent: Sep. 24, 1991

[54] PROCESS FOR 1,1-DICHLORO-1-FLUOROETHANE

[75] Inventor: William H. Gumprecht, Wilmington, Del.

[73] Assignee: E. I. DuPont de Nemours and Company, Wilmington, Del.

[21] Appl. No.: 438,209

[22] Filed: Nov. 20, 1989

Related U.S. Application Data

[63] Continuation of Ser. No. 225,808, Jul. 29, 1988, abandoned.

[51] Int. Cl.$^5$ ............................................. C07C 17/08
[52] U.S. Cl. ..................................... 570/168; 570/166
[58] Field of Search ................................. 570/166, 168

[56] References Cited

U.S. PATENT DOCUMENTS

| | | | |
|---|---|---|---|
| 2,748,177 | 5/1956 | Miller et al. | 570/166 |
| 3,720,722 | 3/1973 | Wada et al. | 570/166 |
| 3,755,477 | 8/1973 | Firth et al. | 260/653.4 |
| 3,803,241 | 4/1974 | Stolkin et al. | 260/593 |
| 3,836,479 | 9/1974 | Paucksch et al. | 252/433 |
| 3,904,701 | 9/1975 | Schultz et al. | 260/653.6 |
| 4,147,733 | 4/1979 | Fiske et al. | 260/653.4 |

FOREIGN PATENT DOCUMENTS

| | | | |
|---|---|---|---|
| 515661 | 8/1955 | Canada | 570/166 |
| 533966 | 12/1956 | Canada | 570/166 |
| 1246703 | 8/1967 | Fed. Rep. of Germany | 570/166 |
| 770640 | 3/1957 | United Kingdom | 570/166 |

*Primary Examiner*—Alan Siegel

[57] ABSTRACT

An improved process for preparing 1,1-dichloro-1-fluoroethane by hydrogen fluoride addition, in the vapor phase, to 1,1-dichloroethylene in the presence of an aluminum fluoride catalyst.

9 Claims, No Drawings

PROCESS FOR 1,1-DICHLORO-1-FLUOROETHANE

This application is a continuation of application Ser. No. 07/225,808 filed July 29, 1988 now abandoned.

FIELD OF THE INVENTION

An improved process for preparing 1,1-dichloro-1-fluoroethane by hydrogen fluoride addition, in the vapor phase, to 1,1-dichloroethylene in the presence of an aluminum fluoride catalyst.

BACKGROUND OF THE INVENTION

Concerns over the theoretical role of certain chlorofluorocarbons (CFC's) in the depletion of the stratospheric ozone layer have increased interest in developing hydrogen-containing chlorofluorocarbons (HCFC's) to replace the suspect CFC's.

One such alternative HCFC which may be used as a solvent, such as in cleaning electronic circuit boards, as a blowing agent for the manufacture of polymer foams, as an aerosol propellant and the like and which is expected to have little or no effect upon the stratospheric ozone layer is 1,1-dichloro-1-fluoroethane ($CH_3CCl_2F$, HCFC-141b), a compound which has an atmospheric boiling point of about 32° C.

1,1-Dichloro-1-fluoroethane is a known compound which has been prepared by a number of known methods. One such method is by the halogen exchange reaction of 1,1,1-trichloroethane with hydrogen fluoride, usually in the presence of a halogen exchange catalyst. Such a reaction may be represented by Equation I,

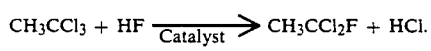

$$CH_3CCl_3 + HF \xrightarrow{\text{Catalyst}} CH_3CCl_2F + HCl. \quad (I)$$

While the reaction as shown in Equation I proceeds very readily, there are several disadvantages to the reaction if it were to be used industrially. One such disadvantage is that, for each molecule of 1,1-dichloro-1-fluoroethane produced, one molecule of hydrogen chloride is also generated which must be recovered and disposed of. Another disadvantage is that the trichloromethyl group of 1,1,1-trichloroethane reacts so readily in the halogen exchange reaction that multiple fluorination almost always occurs under normal reaction conditions. Thus, under conditions favorable for the formation of 1,1-dichloro-1-fluoroethane ($CH_3CCl_2F$), 1-chloro-1,1-difluoroethane ($CH_3CClF_2$) and 1,1,1-trifluoroethane ($CH_3CF_3$) are formed at the expense of $CH_3CCl_2F$, together with the corresponding increase in the formation of hydrogen chloride.

Another reaction to prepare 1,1-dichloro-1-fluoroethane involves hydrogen fluoride addition to 1,1-dichloroethylene (vinylidene chloride) as represented by Equation (II).

$$CH_2=CCl_2 + HF \rightarrow CH_3CCl_2F \quad (II).$$

The reaction as represented by Equation (II) appears to be ideal for the preparation of 1,1-dichloro-1-fluoroethane provided high yields of 1,1-dichloro-1-fluoroethane are achieved, and the vinylidene chloride is effectively consumed. Note that, in this reaction, hydrogen chloride is not formed. High conversion of vinylidene chloride is necessary since both 1,1-dichloro-1-fluoroethane and vinylidene chloride boil at around 32° C., and separation of these two compounds by conventional methods, such as by distillation, is almost impossible.

In U.S. Pat. No. 3,755,477 Firth et al. disclose a vapor-phase reaction of vinylidene chloride with hydrogen fluoride in the presence of a steam-treated chromium oxide catalyst. The disclosure indicates that, at 70°-80° C. reaction temperature, 45 percent of the fluorinated products was 1,1-dichloro-1-fluoroethane while the remainder were more highly fluorinated products, namely, 1-chloro-1,1-difluoroethane and 1,1,1-trifluoroethane. At 90° C.-100° C. reaction temperature, no 1,1-dichloro-1-fluoroethane was reported to be produced.

In U.S. Pat. No. 3,836,479 Paucksch et al. disclose the preparation of a high surface area aluminum fluoride catalyst by admixing boron oxide with alumina, shaping the mixture, and thereafter treating the shaped catalyst with hydrogen fluoride. The thus-prepared catalyst is claimed to be of high activity in catalyzing the hydrogen fluoride addition to double or triple bond compounds. Paucksch et al. teach at Col. 5, lines 35-51, that the claimed catalysts are especially active in hydrogen fluoride addition to olefins which contain one or more fluorine atoms, such as vinyl fluoride, vinylidene fluoride or tetrafluoroethylene, the reaction starting without any external heat and that, at 40°-100° C., 100% conversion to hydrofluorinated compounds is obtained. However, when the olefin contains chlorine or bromine, such as trichloroethylene, 1,1-dichloroethylene, tribromoethylene or 1,1-dibromoethylene, reaction temperatures of between 150° C. to 500° C. are necessary. This teaching is illustrated in Examples 12-15 which show that, while the reaction of hydrogen fluoride with vinyl fluoride, vinylidene fluoride or tetrafluoroethylene proceed with 100% conversion of the olefins at 55°-60° C., the hydrogen fluoride addition to vinyl chloride required a temperature of 175° C. with only 28% conversion of vinyl chloride.

In U.S. Pat. No. 3,803,241 Stolkin et al. disclose a hydrofluorination catalyst prepared by impregnating vacuum-dried alumina with a chromium salt solution and then activating with a stream of hydrogen fluoride at a temperature below 250° C. Preparative reactions are carried out with excess hydrogen fluoride at 140°-400° C. In Example 1 it is shown that, by the use of this catalyst in the vapor-phase reaction of vinylidene chloride and hydrogen fluoride at 198° C., the product obtained was 98.8 volume-percent 1,1,1-trifluoroethane and only 0.2 volume-percent 1,1-dichloro-1-fluoroethane.

In U.S. Pat. No. 3,904,701 Schultz et al. disclose a hydrofluorination catalyst prepared as in the above cited U.S. Pat. No. 3,803,241 with the exception that the alumina, before treatment with hydrogen fluoride, is impregnated with a bismuth salt solution. In Example 1 the claimed catalyst is used in the vapor-phase reaction of hydrogen fluoride with vinylidene chloride, the reaction temperature being 198° C. to 210° C. The products obtained consisted of 99.7 volume-percent $CH_3CF_3$, 0.2 volume-percent $CH_3CF_2Cl$ and 0.1 volume-percent $CH_2=CCl_2$. The presence of 1,1-dichloro-1-fluoroethane is not mentioned.

In U.S. Pat. No. 4,147,733 Fiske et al. disclose vapor-phase reaction of aqueous hydrogen fluoride with vinylidene chloride in the presence of a metal fluoride catalyst which is an admixture of aluminum fluoride, chromium fluoride and nickel fluoride at 250° C. to 415° C., wherein conversion of vinylidene chloride to fluorinated products is extremely low—2% at 250° C. and 13.5% at 415° C. There is no mention of 1,1-dichloro-1-fluoroethane as one of the products formed.

It is an object of the present invention to provide an improved process for the preparation of 1,1-dichloro-1-fluoroethane. It is a further object of the present invention to provide a process for the preparation of 1,1-dichloro-1-fluoroethane by hydrogen fluoride addition to 1,1-dichloroethylene providing said 1,1-dichloro-1-fluoroethane in high yields and purity.

SUMMARY OF THE INVENTION

A process has been discovered for producing 1,1-dichloro-1-fluoroethane comprising contacting a mixture of 1,1-dichloroethylene and anhydrous hydrogen fluoride, in the vapor phase, in the presence of an aluminum fluoride catalyst at a temperature up to about 120° C. to form a reaction stream and, thereafter, separating the 1,1-dichloro-1-fluoroethane from the reaction stream.

DETAILS OF THE INVENTION

The present invention process achieves high yields of 1,1-dichloro-1-fluoroethane combined with minimal formation of polyfluorinated products, high boilers and tars.

The catalyst used in the present process is an aluminum fluoride catalyst. By aluminum fluoride catalyst is meant an aluminum fluoride which may be used in hydrogen fluoride addition to unsaturated compounds or in halogen exchange reactions of halocarbons with hydrogen fluoride. The catalyst can be prepared by treating any aluminum-containing compound capable of being converted to aluminum fluoride by contacting the compound with a vaporizable fluorine-containing compound such as HF, $SF_4$, $CCl_3F$, $CCl_2F_2$, $CHF_3$ or $CCl_2FCClF_2$. By vaporizable fluorine-containing compound is meant a compound which, when passed over the aluminum compound, will convert the aluminum compound to essentially aluminum fluoride.

For example, the catalyst of the instant invention can be prepared by treating aluminum chloride, aluminum bromide or alumina with hydrogen fluoride until the aluminum chloride, aluminum bromide or alumina is converted essentially into aluminum fluoride. It is recognized that, in the act of such a treatment, conversions are usually not complete, that is, there may be some chloride or bromide left when the aluminum fluoride is prepared from aluminum chloride or aluminum bromide, or when prepared from alumina, there may be some oxyfluorides or hydroxyfluorides present. The procedure generally used to prepare the aluminum fluoride catalyst is to treat aluminum chloride, aluminum bromide or alumina with hydrogen fluoride which is initially diluted with a dry inert gas such as nitrogen and, thereafter, to increase the concentration of hydrogen fluoride until 100% hydrogen fluoride is used. The treatment temperature may be raised to facilitate the conversion, say, up to about 500° C. Aluminum chloride or aluminum bromide is usually converted to aluminum fluoride very readily so that high temperatures are not necessary; high temperatures are undesirable with aluminum chloride because of its tendency to sublime. An aluminum fluoride catalyst may also include minor amounts of other metal fluorides admixed therein, such as fluorides of nickel, chromium, cobalt and the like. Such aluminum fluorides containing other metal fluorides are usually prepared by impregnating alumina with appropriate metal salt solutions followed by drying and treatment with hydrogen fluoride as described. The term "aluminum fluoride catalyst" as used herein and in the appended claims include normal fluorides, chlorofluorides, bromofluorides, oxyfluorides, hydroxyfluorides as well as aluminum fluorides containing minor amounts of other metal fluorides.

The vapor-phase reaction of 1,1-dichloroethylene and hydrogen fluoride can be conducted at about 45° C. to about 120° C., preferably from about 50° C. to about 100° C., most preferably from about 55° C. to about 95° C. At temperatures below about 45° C., while the reaction will proceed, the reaction rate is considered to be too slow to make the process industrially practical. At temperatures above about 120° C. the formation of polyfluorinated products, i.e. $CH_3CClF_2$ and $CH_3CF_3$, will increase. In the preferred temperature ranges, both the conversion of 1,1-dichloroethylene and the yield and purity of 1,1-dichloro-1-fluoroethane are enhanced.

The contact time with the catalyst can vary widely and is generally from about 0.5 to 60 seconds, preferably about 1 to 30 seconds.

The amount of hydrogen fluoride relative to 1,1-dichloroethylene in the reactant mixture should be at least stoichiometric, i.e. one mole of hydrogen fluoride per mole of 1,1-dichloroethylene. However, for increased conversion of 1,1-dichloroethylene, a higher ratio of hydrogen fluoride to 1,1-dichloroethylene can be used, say, from about 1.5 to about 10, preferably from about 4 to about 8. Generally, the higher the temperature of the reaction the lower should be the hydrogen fluoride to 1,1-dichloroethylene ratio to minimize polyfluorinated products. In the preferred temperature range of about 55° C. to about 95° C. the preferred hydrogen fluoride to 1,1-dichloroethylene ratio is from about 4 to about 8. Hydrogen fluoride used in the present process can be commercially-available anhydrous hydrogen fluoride.

In carrying out the process of the present invention, the aluminum fluoride catalyst can be preformed or preferably prepared in situ in a suitable reaction vessel by treating either aluminum chloride, aluminum bromide or alumina as described above.

1,1-Dichloroethylene and hydrogen fluoride are preferably premixed in the vapor phase and passed over or through the aluminum fluoride catalyst at the reaction temperature. The mixture of 1,1-dichloroethylene and hydrogen fluoride may also contain some inert gas, such as nitrogen, if desired.

The product stream, consisting primarily of 1,1-dichloro-1-fluoroethane with samll amounts of 1-chloro-1,1-difluoroethane and unreacted 1,1-dichloroethylene plus excess hydrogen fluoride, is collected and purified to recover the hydrogen fluoride for recycle and obtain the 1,1-dichloro-1-fluoroethane. The hydrogen fluoride can be separated by fractional distillation or by cooling and phase-separation from the organic products.

Since 1,1-dichloroethylene has essentially the same boiling point as 1,1-dichloro-1-fluoroethane, it cannot be separated by distillation but, since it is present in the product stream in relatively small amounts in the process of this invention, it can be removed by oxidation with an aqueous alkaline permanganate solution or by brominating it with bromine to form the higher-boiling dibromo derivative.

Pressure is not critical in the present invention process. Subatmospheric, atmospheric or superatmospheric pressures may be used but for convenience, atmospheric or slightly superatmospheric pressures are preferred provided the reactants and products remain in the vapor phase.

EXAMPLE 1

A one-half inch diameter, 10 inch long water-jacketed stainless steel tube having a support screen was charged with 33 g. anhydrous aluminum chloride as 5-15 mesh granules. The tube was then mounted vertically, and water at about 6° C. was circulated through the jacket. Anhydrous hydrogen fluoride gas mixed with nitrogen was passed through the aluminum chloride bed until hydrogen chloride was no longer detected with silver nitrate solution in the exit gas stream.

The aluminum fluoride catalyst thus prepared was then heated by circulating water at about 55° C. in the jacket. A gaseous mixture of hydrogen fluoride and 1,1-dichloroethylene diluted with about 2.5 mole percent nitrogen was passed through the aluminum fluoride bed for 12 hours during which period 455 g. (4.69 moles) of 1,1-dichloroethylene was fed. The mole ratio of hydrogen fluoride to 1,1-dichloroethylene averaged 7.6/1. Contact time of the mixture with the aluminum fluoride averaged 0.75 second. The exit gas was scrubbed in 20.7% aqueous hydrochloric acid at −60° C. to remove excess hydrogen fluoride and to condense the organic products. Periodic gas chromatographic analysis of the organic products over the 12 hour reaction period indicated that 91.9% to 95.6% was the desired 1,1-dichloro-1-fluoroethane, about 0.02% was 1-chloro-1,1-difluoroethane, and 4.3% to 8.1% 1,1-dichloroethylene remained unreacted. The desire 1,1-dichloro-1-fluoroethane was purified by adding a slight excess, as indicated by color, of bromine to the organic products to tie up 1,1-dichloroethylene as the dibromide, followed by washing with an aqueous sodium sulfite solution, then with water, drying and finally distillation.

The aluminum fluoride catalyst left after the above reaction was purged of acids and products with nitrogen gas to provide a granular white solid; no tar build-up was evident. Analysis of the used catalyst indicated 61.4% fluoride, and X-ray fluorescence detected traces of chloride.

EXAMPLE 2

A 3 inch internal diameter by 5 foot long "Inconel" reactor, fitted with a gas feed system and external heaters, was filled with about 10 pounds of alumina as 1/16"×¼-⅜" extrudate. The alumina bed was purged with dry nitrogen while heating to 100° C. The gas feed was switched to a mixture of about 3 pph of dry air and 0.1 pph of anhydrous HF. The introduction of the HF caused a temperature rise up to 200° C. to move through the bed. The temperature was stabilized, and additional air/HF mixture was fed to raise the bed temperature in stages to 300° C. and then to 400°C. The gas feed was then switched to HF diluted with dry nitrogen. The nitrogen feed was gradually decreased until pure HF was fed to the bed between 400°-500° C. the entire activation took several days.

The reactor containing the aluminum fluoride catalyst was connected to a pressure regulator followed by a caustic scrubbing system. The reactor pressure was set at about 45 psig with the regulator, and the bed temperature was lowered to 74° C. A mixture of HF at 5.2 lbs (118 moles) per hour and vinylidene chloride at 6.1 lbs (28.5 moles) per hour was fed as a gas to the catalyst bed. The molar HF/vinylidene chloride ratio was 4.13. A temperature rise occured in the bed so that the temperature ranged from 74° to 86° C. The crude product stream exiting the system was scrubbed in 5% potassium hydroxide solution to remove acids. The isolated organic product consisted of 99.8% 1,1-dichloro-1-fluoroethane, 0.1% 1-chloro-1,1-difluoroethane and 0.1% unreacted vinylidene chloride. This mixture was collected at a rate of about 6.6 pph, corresponding to an 89.6% yield of 1,1-dichloro-1-fluoroethane.

I claim:

1. A process for preparing 1,1-dichloro-1-fluoroethane comprising contacting 1,1-dichloroethylene and anhydrous hydrogen fluoride, in the vapor phase, with an aluminum fluoride catalyst at a reaction temperature from about 55° C. to about 95° C. to produce a product stream and, thereafter, recovering 1,1-dichloro-1-fluorethane from the product stream.

2. The process of claim 1 wherein said 1,1-dichloroethylene and hydrogen fluoride is a mixture comprising from one to about ten moles of hydrogen fluoride per mole of 1,1-dichloroethylene.

3. The process of claim 2 wherein said mixture of 1,1-dichloroethylene and hydrogen fluoride is a mixture comprising from about 4 to about 8 moles of hydrogen fluoride per mole of 1,1-dichloroethylene.

4. The process of claim 1 wherein said aluminum fluoride catalyst is an aluminum fluoride prepared by treating anhydrous aluminum chloride or aluminum bromide with a vaporizable fluorine-containing compound.

5. The process of claim 4 wherein said mixture of 1,1-dichloroethylene and hydrogen fluoride is a mixture comprising from about 4 to about 8 moles of hydrogen fluoride per mole of 1,1-dichloroethylene.

6. The process of claim 1 wherein said aluminum fluoride catalyst is an aluminum fluoride prepared by treating alumina with a vaporizable fluorine-containing compound.

7. The process of claim 6 wherein said mixture of 1,1-dichloroethylene and hydrogen fluoride is a mixture comprising from about 4 to about 8 moles hydrogen fluoride per mole of 1,1-dichloroethylene.

8. The process of claim 1 wherein said aluminum fluoride catalyst is an aluminum fluoride prepared by treating alumina impregnated with at least one compound of nickel, chromium or cobalt with a vaporizable fluorine-containing compound.

9. The process of claim 8 wherein said mixture of 1,1-dichloroethylene and hydrogen fluoride is a mixture comprising from about 4 to 8 moles of hydrogen fluoride per mole of 1,1-dichloroethylene.

* * * * *